US012751819B2

(12) United States Patent
Ma et al.

(10) Patent No.: US 12,751,819 B2
(45) Date of Patent: Oct. 6, 2026

(54) BALLOON EXPANDABLE INTERVENTIONAL VALVE STENT HAVING INWARDLY-NARROWED WING-SPREADING SKIRT

(71) Applicant: NANJING SAINT MEDICAL TECHNOLOGY CO., LTD., Nanjing (CN)

(72) Inventors: Chenming Ma, Nanjing (CN); Jiajia Gu, Nanjing (CN)

(73) Assignee: NANJING SAINT MEDICAL TECHNOLOGY CO., LTD., Nanjing (CN)

( * ) Notice: Subject to any disclaimer, the term of this patent is extended or adjusted under 35 U.S.C. 154(b) by 566 days.

(21) Appl. No.: 18/264,176

(22) PCT Filed: Dec. 14, 2021

(86) PCT No.: PCT/CN2021/137952
§ 371 (c)(1),
(2) Date: Aug. 3, 2023

(87) PCT Pub. No.: WO2022/151891
PCT Pub. Date: Jul. 21, 2022

(65) Prior Publication Data

US 2024/0099833 A1 Mar. 28, 2024

(30) Foreign Application Priority Data

Jan. 14, 2021 (CN) ........................ 202110051090.7

(51) Int. Cl.
*A61F 2/24* (2006.01)

(52) U.S. Cl.
CPC .......... *A61F 2/2418* (2013.01); *A61F 2/2433* (2013.01); *A61F 2220/0025* (2013.01)

(58) Field of Classification Search
CPC ................. A61F 2/2418; A61F 2/2433; A61F 2220/0025; A61F 2250/0039; A61F 2250/0069
See application file for complete search history.

(56) References Cited

U.S. PATENT DOCUMENTS

2014/0277423 A1 9/2014 Alkhatib et al.
2017/0189174 A1 7/2017 Braido et al.
(Continued)

FOREIGN PATENT DOCUMENTS

CN 103705315 A 4/2014
CN 108430394 A 8/2018
(Continued)

*Primary Examiner* — Richard G Louis
(74) *Attorney, Agent, or Firm* — NKL Law; Allen Xue

(57) ABSTRACT

A balloon expandable interventional valve stent has a stent main body (1), leaflets and a wing-spreading skirt (2). The wing-spreading skirt (2) is arranged outside an outflow channel (4), and several round holes (8) are evenly arranged at the edge of the wing-spreading skirt (2) close to the outflow channel (4) A pulling suture (5) is connected to the wing-spreading skirt (2). When the balloon (7) is expanded and spread, the pulling suture (5) connected to the skirt on an inflow channel (3) side is gradually tightened in the circumferential direction under the effect of the expansion force of the balloon (7), so that the wing-spreading skirt (2) is folded in the axial direction of the stent to the outside of the inflow channel (3) to form portions protruding outwards in the radial direction of the stent main body (1), so as to cover or occlude a paravalvular leak.

8 Claims, 3 Drawing Sheets

(56) References Cited

U.S. PATENT DOCUMENTS

| | | | | |
|---|---|---|---|---|
| 2017/0224482 | A1 | 8/2017 | Para | |
| 2017/0273784 | A1 | 9/2017 | Racchini et al. | |
| 2018/0008402 | A1 | 1/2018 | Braido et al. | |
| 2020/0315790 | A1 * | 10/2020 | Krivoruchko | A61F 2/2418 |

FOREIGN PATENT DOCUMENTS

| | | | |
|---|---|---|---|
| CN | 108834399 | A | 11/2018 |
| CN | 109419572 | A | 3/2019 |
| CN | 110711052 | A | 1/2020 |
| CN | 111132634 | A | 5/2020 |
| CN | 215130896 | U | 12/2021 |

* cited by examiner

BALLOON EXPANDABLE INTERVENTIONAL VALVE STENT HAVING INWARDLY-NARROWED WING-SPREADING SKIRT

CROSS-REFERENCE TO RELATED APPLICATIONS

This application is a U.S. national stage entry of PCT International Application No. PCT/CN2021/137952, filed on Dec. 14, 2021, which claims priority to Patent Application No. 202110051090.7 filed with China National Intellectual Property Administration on Jan. 14, 2021 and entitled "BALLOON EXPANDABLE INTERVENTIONAL VALVE STENT HAVING INWARDLY-NARROWED WING-SPREADING SKIRT", the content of which is incorporated herein by reference in its entirety.

TECHNICAL FIELD

The present disclosure belongs to the field of medical devices, and particularly relates to a balloon-expandable interventional valve stent with an inwardly-narrowed wing-spreading skirt, which can be applied to aortic valve, pulmonary valve, mitral valve and tricuspid valve positions, damaged biological valve, valve in valve, and other scenarios.

BACKGROUND

Paravalvular leak (PVL), i.e., a leak formed between an artificial valve and surrounding tissues, is a common and serious complication in all heart valve surgeries, particularly the incidence of which is extremely high in transcatheter valve therapies that are currently becoming more prevalent. Several studies have shown that postsurgical paravalvular leaks are directly related to the degree of recovery, reoperation rate, hospital readmission rate, and early-, medium-, and long-term mortality of a patient.

A meta-analysis of several international studies has shown that only 6%-59% of patients after the transcatheter aortic valve interventional surgery did not develop paravalvular leaks. In addition to unavoidable reasons such as the inability to remove the patient's original degenerated, decayed, or damaged valves, and the patient's own anatomical structures such as a non-circular valve annulus plane and other factors, the reasons for this are also closely related to the design characteristics of the current transcatheter valve interventional surgical equipment. With the popularization of transcatheter technology all over the world, more patients, especially younger patients, will choose transcatheter valve surgery to receive treatment, and the emergence of novel transcatheter valve interventional surgical equipment is imperative.

Currently, the existing balloon-expandable interventional valve is usually provided with a skirt on the outer side of an inflow channel, such as the artificial valve structure disclosed in Patent Document CN108430394A, and such structure is designed based on years of clinical experience, and it is considered that the paravalvular leak can be improved by increasing the contact area with the heart valve annulus plane. However, the existing valve structure still has a problem in that the effectiveness of paravalvular leak prevention is limited because the size of the valve delivery system cannot be made too large, resulting in the skirt not being able to be infinitely thickened. Therefore, there is a need for an interventional valve that can prevent the paravalvular leak without increasing the size of the valve delivery system.

SUMMARY

Therefore, an object of the present disclosure is to provide a balloon-expandable interventional valve stent with an inwardly-narrowed wing-spreading skirt. According to a special design, an inwardly-narrowed wing-spreading skirt is arranged on an outflow channel of a stent, and the wing-spreading skirt can extend radially outwards from the stent to cover and occlude a paravalvular leak, so that adverse effects caused by the paravalvular leak are prevented.

The present disclosure is implemented by the following technical schemes:

The present disclosure provides a balloon-expandable interventional valve stent with an inwardly-narrowed wing-spreading skirt, comprising a stent main body, a valve leaflet, and a wing-spreading skirt, wherein the stent main body comprises an inflow channel positioned at a lower portion and an outflow channel positioned at an upper portion, the wing-spreading skirt is arranged on an outer side of the outflow channel, the side of the wing-spreading skirt close to a middle portion of the stent main body is fixedly connected to the stent, other portions of the wing-spreading skirt are not fixedly connected to the stent main body, and the surface of the wing-spreading skirt is attached to the surface of the stent main body; an inflow channel side of the stent main body is also provided with a skirt; a pulling suture is connected to the wing-spreading skirt, one side of the pulling suture is connected to the wing-spreading skirt, the other side is connected to the skirt on the inflow channel side, and the pulling suture is connected between the wing-spreading skirt and the skirt on the inflow channel side in a reciprocating manner for multiple times; when a balloon is expanded and spread, two ends of the stent main body are firstly spread, and the middle portion of the stent main body is subsequently spread; when the stent main body on the inflow channel side is spread, the skirt on the inflow channel side is unfolded, and the pulling suture connected to the skirt on the inflow channel side is gradually tightened in a circumferential direction under the action of an expansion force of the balloon, such that the pulling suture in the wing-spreading skirt on an outflow channel side is tensioned, and the tensioned pulling suture causes the wing-spreading skirt to be folded towards an outer side of the inflow channel in an axial direction of the stent main body to form a portion protruding outwards in a radial direction of the stent main body, thereby covering or occluding a paravalvular leak. According to the valve stent described herein, several round holes are evenly arranged at an edge position of the wing-spreading skirt close to the outflow channel side, and the number of the round holes is even.

According to the valve stent described herein, the whole pulling suture is in a plurality of continuous shapes like a Chinese character "ji (几)", a plurality of connecting points are arranged at intervals on the skirt of the inflow channel side to connect the pulling suture, the pulling suture sequentially passes through each of the connecting points and each of the round holes in the order of "connecting point-round hole-round hole-connecting point", and when the pulling suture is tensioned, the wing-spreading skirt on the outflow channel side is folded towards the outer side of the inflow channel in the axial direction of the stent.

According to the valve stent described herein, the number of the pulling suture is 1, 2, 3, 4, 6, or 12, preferably 1, and the pulling suture continuously passes through the round holes in the wing-spreading skirt and the plurality of connecting points on the skirt of the inflow channel side.

According to the valve stent described herein, when there are 2 or more pulling sutures, the 2 or more pulling sutures described above have equal length to each other, are connected end to end in succession at the connecting points of the skirt on the inflow channel side, and jointly cover the whole circumference of the wing-spreading skirt.

According to the valve stent described herein, the wing-spreading skirt and the pulling suture are both made of a flexible non-metallic material.

According to the valve stent described herein, the pulling suture is made of a polymer material, preferably polyglycolic acid, polylactic acid, or poly(p-dioxanone).

The beneficial effects of the present disclosure are as follows:

The present disclosure has an advantage that the structure of the outflow channel is fully utilized, such that the wing-spreading skirt that can be used is increased on the premise of not increasing the diameter of a delivery system. For the paravalvular leak, such as a non-elliptical heart valve annulus, the wing-spreading skirt can provide a superior occlusion effect relative to the current prior art. Moreover, because of the use of flexible non-metallic materials, the additional structure does not increase damage to the heart.

DETAILED DESCRIPTION

The present disclosure will be further illustrated with reference to the following specific examples. It should be understood that these examples are merely intended to illustrate the present disclosure rather than limit the protection scope of the present disclosure. In addition, it should be understood that various changes or modifications may be made by those skilled in the art after reading the teachings of the present disclosure, and these equivalents also fall within the protection scope of the present disclosure.

Figure 1:
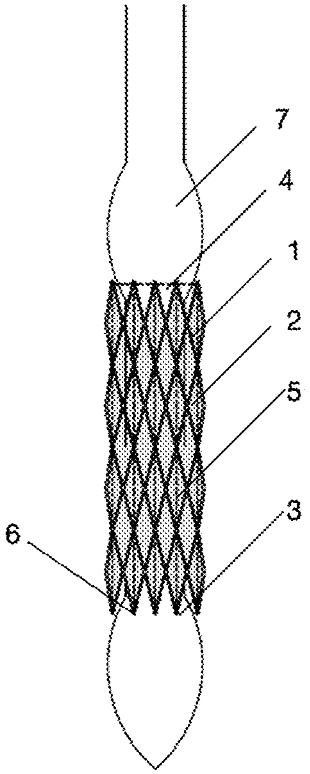
FIG. 1 is a schematic view of a balloon-expandable interventional valve stent in a compressed state according to an embodiment of the present disclosure.
Figure 2:
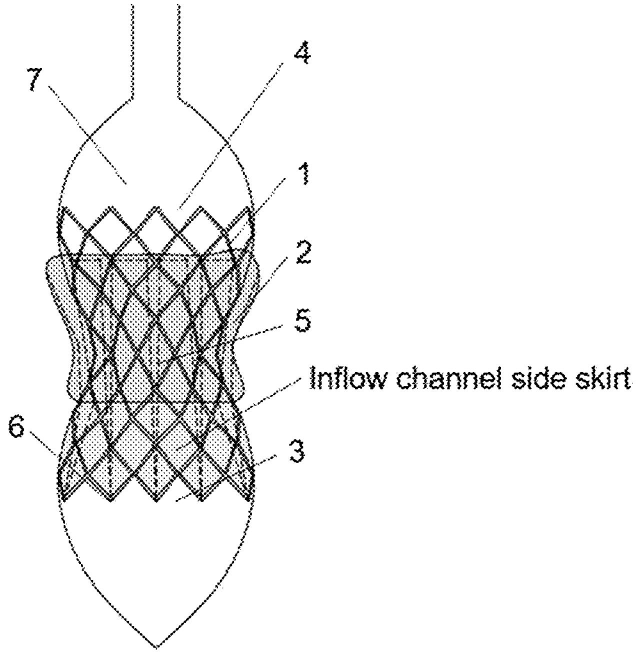
FIG. 2 is a schematic view of the balloon-expandable interventional valve stent during an expansion process according to an embodiment of the present disclosure.
Figure 3:
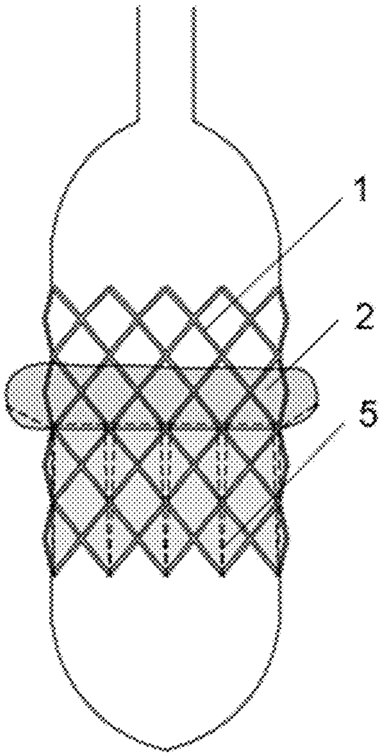
FIG. 3 is a schematic view of the balloon-expandable interventional valve stent in an expanded state according to an embodiment of the present disclosure.
Figure 4:
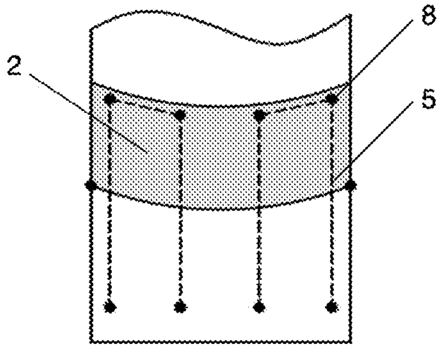
FIG. 4 is a schematic view of pulling sutures of the balloon-expandable interventional valve stent according to an embodiment of the present disclosure.

As shown in FIGS. 1-3, a balloon-expandable interventional valve stent comprises a stent main body 1, a valve leaflet (not shown), and a wing-spreading skirt 2, wherein the stent main body 1 comprises an inflow channel 3 positioned at a lower portion and an outflow channel 4 positioned at an upper portion, the wing-spreading skirt 2 is arranged on an outer side of the outflow channel 4, the side of the wing-spreading skirt 2 close to a middle portion of the stent main body 1 is fixedly connected to the stent main body 1, other portions are not fixed, and the surface of the wing-spreading skirt 2 is attached to the surface of the stent main body 1. Several round holes 8 are evenly arranged at an edge position of the wing-spreading skirt 2 close to an outflow channel side, and the number of the round holes is even; a pulling suture 5 is connected to the wing-spreading skirt 2.

An inflow channel side of the stent main body 1 is also provided with a skirt, and a plurality of connecting points 6 are arranged at intervals on the skirt of the inflow channel side to connect the pulling suture 5. The pulling suture 5 is in a plurality of continuous shapes like a Chinese character "ji (几)", and sequentially passes through each of the connecting points 6 and each of the round holes 8 in the order of "connecting point-round hole-round hole-connecting point". There can be several pulling sutures, for example, 1, 2, 3, 4, 6, or 12 pulling sutures, preferably 1 pulling suture, and the pulling suture continuously passes through the round holes 8 in the wing-spreading skirt and the plurality of connecting points 6 on the outer skirt of the inflow channel side; when there are 2 or more pulling sutures, the 2 or more pulling sutures 5 described above have equal length to each other, are connected end to end in succession at the connecting points 6, and jointly cover the whole circumference of the wing-spreading skirt 2.

When a balloon 7 is expanded and spread, two ends of the stent main body 1 are firstly spread, and the middle portion of the stent main body 1 is subsequently spread; when the stent main body 1 on the inflow channel side is spread, the skirt on the inflow channel side is unfolded, the pulling suture 5 connected to the skirt on the inflow channel side is gradually tightened in a circumferential direction under the action of an expansion force of the balloon, such that the pulling suture 5 in the wing-spreading skirt 2 on the outflow channel side is tensioned, causing the wing-spreading skirt 2 on the outflow channel side to be folded towards an outer side of the inflow channel in an axial direction of the stent main body 1, the wing-spreading skirt in the folded state presents a protruding portion outwards in the radial direction of the stent main body 1 under the combined action of the expansion force of the balloon and the tension force of the pulling suture, and the skirt portion protruding outwards in the radial direction can cover and occlude a paravalvular leak and integrally form the inwardly-narrowed wing-spreading skirt 2. The wing-spreading skirt 2 is made of a flexible non-metallic material, and the pulling suture 5 can be made of a polymer material such as polyglycolic acid, polylactic acid, poly(p-dioxanone), or the like.

Figure 5:
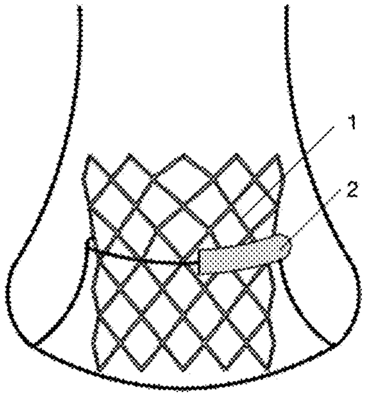
FIG. 5 is a front view of an effect view of the balloon-expandable interventional valve stent of the present disclosure.
Figure 6:
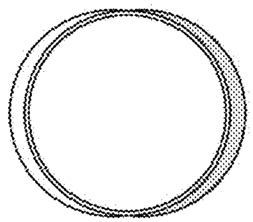
FIG. 6 is a top view of the effect view of the balloon-expandable interventional valve stent of the present disclosure.

As can be seen from FIGS. 5 and 6, the technical scheme of the present disclosure makes full use of the structure of the outflow channel, such that the wing-spreading skirt that can be used is increased on the premise of not increasing the diameter of a delivery system. The wing-spreading skirt structure of the present disclosure can greatly improve the occlusion effect on the paravalvular leak. Moreover, because of the use of flexible non-metallic materials, the additional structure does not increase damage to the heart.

The embodiments of the present disclosure have been described above. However, the present disclosure is not limited to the embodiments described above. Any modification, equivalent, improvement, and the like made without departing from the spirit and principle of the present disclosure shall fall within the protection scope of the present disclosure.

The invention claimed is:

1. A balloon-expandable interventional valve stent, comprising a stent main body, a valve leaflet, and a wing-spreading skirt, wherein:

the stent main body comprises an inflow channel positioned at a lower portion and an outflow channel positioned at an upper portion, the wing-spreading skirt is arranged on an outer side of the outflow channel, a portion of the wing-spreading skirt proximate to a middle portion of the stent main body is fixedly connected to the stent, and a surface of the wing-spreading skirt is attached to the surface of the stent main body;

an inflow channel side of the stent main body is further provided with a skirt;

a pulling suture connecting the wing-spreading skirt and the skirt on the inflow channel side and extending between the wing-spreading skirt and the skirt on the inflow channel side in a reciprocating manner for multiple times;

when a balloon is expanded and spread within the balloon-expandable interventional valve stent, two ends of the stent main body are firstly spread, and the middle portion of the stent main body is subsequently spread;

when the stent main body on the inflow channel side is spread, the skirt on the inflow channel side unfolds, and the pulling suture connected to the skirt on the inflow channel side tightens in a circumferential direction under the action of an expansion force of the balloon, such that the pulling suture in the wing-spreading skirt on an outflow channel side is tensioned, and the tensioned pulling suture causes the wing-spreading skirt to protrude outwardly in a radial direction from the stent main body, thereby covering or occluding a paravalvular leak when deployed to a treatment site.

2. The balloon-expandable interventional valve stent according to claim 1, wherein an even number of a plurality of round holes are arranged at an edge position of the wing-spreading skirt close to the outflow channel side.

3. The balloon-expandable interventional valve stent according to claim 2, wherein a plurality of connecting points are arranged at intervals on the skirt on the inflow channel side, and each pulling suture alternately passes through the plurality of connecting points and the plurality of round holes in a sequence of from the first connecting point to the first round hole to the second connecting point and so on until the last round hole, such that, when the pulling suture is tensioned, the wing-spreading skirt on the outflow channel side folds towards the outer side of the inflow channel in the axial direction of the stent.

4. The balloon-expandable interventional valve stent according to claim 3, wherein the pulling suture is a single continuous line or has 2, 3, 4, 6, or 12 sections.

5. The balloon-expandable interventional valve stent according to claim 4, wherein the pulling suture has 2 or more sections of equal length that are connected end to end in succession, with each connection point disposed at one of the plurality of connecting points of the skirt on the inflow channel side, and jointly cover the whole circumference of the wing-spreading skirt.

6. The balloon-expandable interventional valve stent according to claim 5, wherein the wing-spreading skirt and the pulling suture are both made of a flexible non-metallic material.

7. The balloon-expandable interventional valve stent according to claim 6, wherein the pulling suture is made of a polymer material.

8. The balloon-expandable interventional valve stent according to claim 6, wherein the pulling suture is made of polyglycolic acid, polylactic acid, or poly(p-dioxanone).

* * * * *